United States Patent [19]
Oppelt

[11] Patent Number: 5,886,223
[45] Date of Patent: Mar. 23, 1999

[54] PROCESS FOR THE PREPARATION OF SUBSTITUTED β-KETOANILIDE COMPOUNDS

[75] Inventor: John C. Oppelt, Bridgewater, N.J.

[73] Assignee: American Cyanamid Company, Madison, N.J.

[21] Appl. No.: 57,309

[22] Filed: Apr. 8, 1998

[51] Int. Cl.$^6$ .................. C07C 233/05; C07C 231/04
[52] U.S. Cl. .................. 564/200; 564/189; 564/190; 564/199; 558/414
[58] Field of Search ................... 564/189, 190, 564/199, 200; 558/414

[56] References Cited

U.S. PATENT DOCUMENTS

| | | | |
|---|---|---|---|
| 1,982,675 | 12/1934 | Law | 564/200 |
| 3,072,724 | 1/1963 | Elam et al. | 564/189 |
| 3,304,328 | 2/1967 | Pelley | 564/200 |

FOREIGN PATENT DOCUMENTS 0105028  4/1984  European Pat. Off. .

OTHER PUBLICATIONS

Barbaro et al, J. Org. Chem., vol. 60, 1020–2025, 1995.
Journal of Organic Chemistry, 26, pp. 4340–4344 (1961).

*Primary Examiner*—Shailendra Kumar
*Attorney, Agent, or Firm*—Charles F. Costello, Jr.

[57] ABSTRACT

There is provided a process for the preparation of substituted β-ketoanilide compounds having the structural formula I

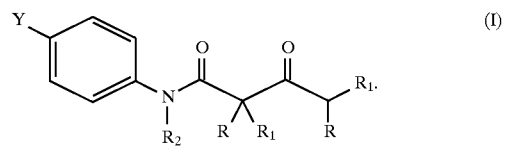

The substituted β-ketoanilide compounds are useful for the control of insect pests.

16 Claims, No Drawings

PROCESS FOR THE PREPARATION OF SUBSTITUTED β-KETOANILIDE COMPOUNDS

BACKGROUND OF THE INVENTION

Substituted β-ketoanilide compounds which are useful for the control of insect pests are described in a related U.S. patent application. The related application discloses that substituted β-ketoanilide compounds may be prepared by reacting a substituted aniline with a lactone such as dimethylketene β-lactone dimer. However, dimethylketene β-lactone dimer is not entirely satisfactory because it is a persistent lachrymator.

U.S. Pat. No. 3,072,724 discloses that certain β-ketoamide compounds may be prepared by reacting a nitrogen containing compound with a tetraalkyl-1,3-cyclobutanedione. However, that patent specifically discloses that aromatic amines such as aniline do not react with tetraalkyl-1,3-cyclobutanediones to form β-ketoamides. In addition, Haske, et al in the Journal of Organic Chemistry, 26, pp. 4340–4344 (1961) disclose that it is difficult to prepare 2,2,4-trimethyl-3-oxovaler-anilide from aniline and tetramethyl-1,3-cyclobutanedione.

It is, therefore, an object of the present invention to provide a new and efficient process for the preparation of substituted β-ketoanilide compounds which avoids the use of dimethylketene β-lactone dimer and overcomes the difficulties described in the art associated with the use of tetraalkyl-1,3-cyclobutanediones.

SUMMARY OF THE INVENTION

The present invention provides a process for the preparation of substituted β-ketoanilide compounds having the structural formula I

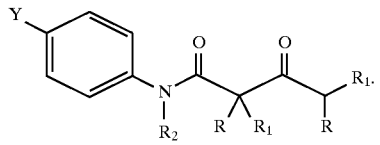

(I)

wherein

R and $R_1$ are each independently $C_1$–$C_4$alkyl or R and $R_1$ are taken together with the carbon atom to which they are attached to form a $C_3$–$C_6$cycloalkyl ring;

$R_2$ is hydrogen or $C_1$–$C_4$alkyl optionally substituted with one $C_1$–$C_4$alkoxy group; and Y is halogen, $C_1$–$C_4$alkyl, $C_1$–$C_4$haloalkyl, $C_1$–$C_4$alkoxy, $C_1$–$C_4$haloalkoxy, nitro or cyano, which process comprises reacting a substituted aniline compound having the structural formula II

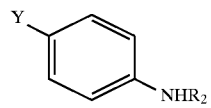

(II)

wherein $R_2$ and Y are as described above with a tetraalkyl-1,3-cyclobutanedione compound having the structural formula III

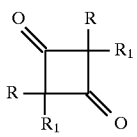

(III)

wherein R and $R_1$ are as described above and a base in the presence of a solvent.

DETAILED DESCRIPTION OF THE INVENTION

The process of the present invention preferably comprises reacting a substituted aniline of formula II with about 0.8 to about 1.5 molar equivalents of a tetraalkyl-1,3-cyclobutanedione of formula III and about 0.8 to about 1.5 molar equivalents of a base in the presence of a solvent at a temperature of from about 15° C. to about 120° C.

Surprisingly, it has been found that substituted β-ketoanilide compounds are prepared in high yield by reacting a substituted aniline with a tetraalkyl-1,3-cyclobutanedione in the presence of a base. Uniquely, the process of the present invention overcomes the difficulties described in the art associated with the use of tetraalkyl-1,3-cyclobutanediones by using a base in the reaction scheme.

Bases suitable for use in the present invention include alkali metal $C_1$–$C_6$alkoxides such as potassium tert-butoxide, sodium tert-butoxide, potassium tert-pentoxide, sodium tert-pentoxide, potassium isopropoxide, sodium isopropoxide, potassium ethoxide, sodium ethoxide, potassium methoxide, sodium methoxide and the like; alkaline earth metal $C_1$–$C_6$alkoxides; alkali metal carbonates such as potassium carbonate and sodium carbonate; alkaline earth metal carbonates such as calcium carbonate; alkali metal hydroxides such as potassium hydroxide and sodium hydroxide; alkaline earth metal hydroxides such as calcium hydroxide; and heterocyclic amines including, but not limited to, pyridine; substituted pyridines such as 2,6-dimethylpyridine, 2-methylpyridine, 3-methylpyridine, 4-methylpyridine and the like; imidazole; substituted imidazoles; quinoline; and substituted quinolines. Preferred bases for use in the process of this invention include alkali metal $C_1$–$C_6$alkoxides and alkali metal carbonates. Potassium tert-butoxide, sodium tert-butoxide, potassium tert-pentoxide, sodium tert-pentoxide, potassium isopropoxide, sodium isopropoxide, potassium carbonate and sodium carbonate are especially suitable for use in the process of the present invention.

In a preferred process of this invention, the base is present in an amount of from about 0.8 to about 1.5 molar equivalents relative to the formula II substituted aniline.

Solvents suitable for use in the process of the present invention include aprotic solvents and tertiary($C_4$–$C_8$) alcohols such as tert-butanol and the like and mixtures thereof. Aprotic solvents particularly suitable for use in the process of this invention include carboxylic acid amides such as N,N-dimethylformamide, N,N-dimethylacetamide and the like; aromatic hydrocarbons such as toluene, benzene, o-xylene, m-xylene, p-xylene, xylene mixtures and the like; halogenated aromatic hydrocarbons such as chlorobenzene, o-dichlorobenzene and the like; halogenated hydrocarbons such as dichloromethane, 1,2-dichloroethane and the like; cyclic ethers such as tetrahydrofuran, 1,3-dioxane, 1,4-dioxane and the like; and mixtures thereof. Preferred solvents include carboxylic acid amides such as N,N-dimethylformamide and N,N-dimethylacetamide; and halogenated hydrocarbons such as dichloromethane and 1,2-dichloroethane. N,N-dimethyl-formamide is especially suitable for use in the process of the present invention.

The process of the present invention is preferably conducted at a temperature of from about 15° C. to about 120° C. and more preferably at a temperature of from about 25° C. to about 100° C.

Conventional phase transfer catalysts such as tetrabutylammonium bromide, tetrabutylammonium iodide, benzyltriethylammonium chloride, tetrabutylammonium hydrogen sulfate and tetramethylammonium chloride may be used in the process of the present invention to enhance the rate of reaction.

The substituted β-ketoanilide compounds of this invention may be isolated by conventional techniques such as dilution of the reaction mixture with water and filtration or, alternatively, extraction with a suitable solvent. In particular, the formula I compounds may be isolated by diluting the reaction mixture with water and collecting the solid formula I compound. In a preferred isolation procedure of this invention, the dilution step is conducted in the presence of a mineral acid such as hydrochloric acid, hydrobromic acid and sulfuric acid.

Exemplary of halogen hereinabove are fluorine, chlorine, bromine and iodine. The term "$C_1$–$C_4$haloalkyl" is defined as a $C_1$–$C_4$alkyl group substituted with one or more halogen atoms.

In a preferred process of the present invention,

R and $R_1$ are each independently $C_1$–$C_4$alkyl;

$R_2$ is hydrogen or $C_1$–$C_4$alkyl optionally substituted with one $C_1$–$C_4$alkoxy group; and Y is halogen, $C_1$–$C_4$alkyl, $C_1$–$C_4$haloalkyl, $C_1$–$C_4$alkoxy, $C_1$–$C_4$haloalkoxy, nitro or cyano.

In a more preferred process of this invention,

R and $R_1$ are methyl;

$R_2$ is hydrogen or $C_1$–$C_4$alkyl; and

Y is halogen or $C_1$–$C_4$haloalkyl.

In a most preferred process of the present invention,

R and $R_1$ are methyl;

$R_2$ is hydrogen or methyl; and

Y is Cl or trifluoromethyl.

The process of the present invention is especially useful for the preparation of α,α,α-trifluoro-2,2,4-trimethyl-3-oxo-p-valerotoluidide; and α,α,α-trifluoro-N,2,2,4-tetramethyl-3-oxo-p-valerotoluidide.

The substituted β-ketoanilide compounds produced by the process of this invention are useful for the control of insect pests. Those compounds are also useful for the protection of plants from damage caused by insect attack and infestation. The substituted β-ketoanilide compounds are especially useful for the control of soil-dwelling Coleoptera pests such as southern corn rootworms, northern corn rootworms, western corn rootworms, and Mexican corn rootworms.

Starting formula II substituted aniline compounds are well known in the art and may be prepared by one of ordinary skill using conventional procedures. In addition, acid addition salts of formula II compounds may be used to generate the formula II compounds used in this invention. If an acid addition salt of a formula II compound is employed, excess base is required to obtain the free base formula II compound.

Tetraalkyl-1,3-cyclobutanedione compounds of formula III are well known in the art and may be prepared according to conventional procedures known in the art (see, e.g., Chem. Ber., 39, page 969 (1906); Chem. Ber., 41, page 2216 (1908); Justus Liebigs Ann. Chem., 401, page 297 (1913); Helv. Chim. Acta, 6, page 296 (1923); J. Org. Chem., 1, pages 137–138 (1936); J. Amer. Chem. Soc., 87, pages 2613–2619 (1965); J. Org. Chem., 31, pages 1931–1934 (1966); J. Amer. Chem. Soc., 106(16), pages 4566–4570 (1984); Indian J. Chem. Sect. B, 23(6), pages 498–501 (1984); J. Org. Chem., 50(12), pages 2105–2109 (1985); and Liebigs Ann. Chem., pages 377–379 (1987)).

In order to facilitate a further understanding of this invention, the following example is presented primarily for the purpose of illustrating more specific details thereof. The scope of the invention should not be deemed limited by the example, but encompasses the entire subject matter defined in the claims.

EXAMPLE 1

Preparation of α,α,α-Trifluoro-2,2,4-trimethyl-3-oxo-p-valerotoluidide

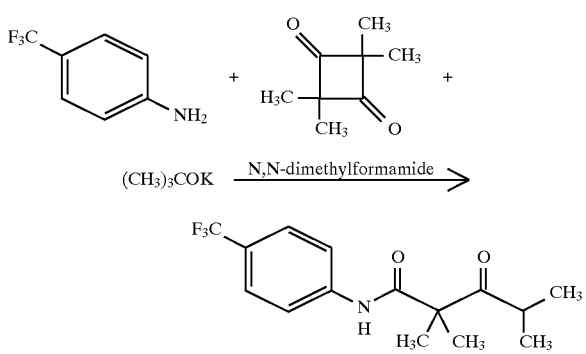

Potassium tert-butoxide (426 g, 3.8 mol) is added over a 40 minute period to a mixture of α,α,α-trifluoromethyl-p-toluidine (564 g, 3.5 mol) and 2,2,4,4-tetramethyl-1,3-cyclobutanedione (504 g, 3.6 mol) in N,N-dimethylformamide (2 L). The reaction mixture temperature rises to 80° C. during the addition. After the addition is complete, the reaction mixture is stirred for 2.3 hours and slowly poured into water (18 L) which contains 300 mL of concentrated hydrochloric acid. The resultant aqueous mixture is stirred for 30 minutes and filtered to obtain a yellow solid. The solid is washed with water, air-dried and dried overnight in a vacuum oven at 60°–65° C. to give the title product as a yellow solid (1,021 g, 96.8% yield) which is identified by $^1$H NMR spectral analysis.

I claim:

1. A process for the preparation of a compound having the structural formula I

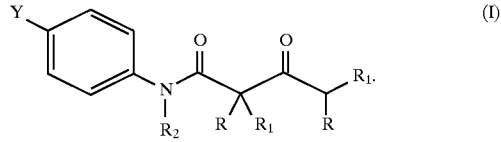

wherein

R and $R_1$ are each independently $C_1$–$C_4$alkyl or R and $R_1$ are taken together with the carbon atom to which they are attached to form a $C_3$–$C_6$cycloalkyl ring;

$R_2$ is hydrogen or $C_1$–$C_4$alkyl optionally substituted with one $C_1$–$C_4$alkoxy group; and Y is halogen, $C_1$–$C_4$alkyl, $C_1$–$C_4$haloalkyl, $C_1$–$C_4$alkoxy, $C_1$–$C_4$haloalkoxy, nitro or cyano, which process comprises reacting a substituted aniline compound having the structural formula II

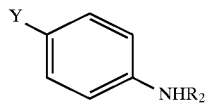

(II)

wherein

R$_2$ and Y are as described above with a tetraalkyl-1,3-cyclobutanedione compound having the structural formula III

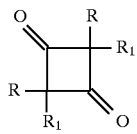

(III)

wherein

R and R$_1$ are as described above and a base in the presence of a solvent.

2. The process according to claim 1 wherein the base is selected from the group consisting of an alkali metal C$_1$–C$_6$alkoxide, an alkaline earth metal C$_1$–C$_6$alkoxide, an alkali metal carbonate, an alkaline earth metal carbonate, an alkali metal hydroxide, an alkaline earth metal hydroxide and a heterocyclic amine.

3. The process according to claim 2 wherein the base is selected from the group consisting of an alkali metal C$_1$–C$_6$alkoxide and an alkali metal carbonate.

4. The process according to claim 3 wherein the base is selected from the group consisting of potassium tert-butoxide, sodium tert-butoxide, potassium tert-pentoxide, sodium tert-pentoxide, potassium isopropoxide, sodium isopropoxide, potassium carbonate and sodium carbonate.

5. The process according to claim 1 wherein the solvent is selected from the group consisting of an aprotic solvent and a tertiary(C$_1$–C$_8$)alcohol and mixtures thereof.

6. The process according to claim 5 wherein the aprotic solvent is selected from the group consisting of a carboxylic acid amide, an aromatic hydrocarbon, a halogenated aromatic hydrocarbon, a halogenated hydrocarbon and a cyclic ether and mixtures thereof.

7. The process according to claim 6 wherein the solvent is selected from the group consisting of a carboxylic acid amide and a halogenated hydrocarbon and mixtures thereof.

8. The process according to claim 7 wherein the solvent is selected from the group consisting of N,N-dimethylformamide, N,N-dimethylacetamide, dichloromethane and 1,2-dichloroethane and mixtures thereof.

9. The process according to claim 1 wherein the temperature of the reaction mixture is about 15° C. to about 120° C.

10. The process according to claim 9 wherein the temperature is about 25° C. to about 100° C.

11. The process according to claim 1 wherein the tetraalkyl-1,3-cyclobtutanedione is present in the amount of about 0.8 to about 1.5 molar equivalents.

12. The process according to claim 1 wherein the base is present in the amount of about 0.8 to about 1.5 molar equivalents.

13. The process according to claim 1 which further comprises a phase transfer catalyst.

14. The process according to claim 1 wherein

R and R$_1$ are each independently C$_1$–C$_4$alkyl.

15. The process according to claim 14 wherein

R and R$_1$ are methyl;

R$_2$ is hydrogen or C$_1$–C$_4$alkyl; and

Y is halen or C$_1$–C$_4$haloalkyl.

16. The process according to claim 15 wherein

R$_2$ is hydrogen or methyl; and

Y is Cl or trifluoromethyl.

* * * * *